(12) United States Patent
Kim et al.

(10) Patent No.: US 10,920,266 B2
(45) Date of Patent: Feb. 16, 2021

(54) DEVICE FOR REAL-TIME MEASUREMENT OF BACTERIA BY ATP DETECTION

(71) Applicant: KOREA INSTITUTE OF SCIENCE AND TECHNOLOGY, Seoul (KR)

(72) Inventors: Byoung Chan Kim, Seoul (KR); Jae Hee Jung, Seoul (KR); Hye Ri Kim, Seoul (KR); Yusung Cho, Seoul (KR); Kang Bong Lee, Seoul (KR)

(73) Assignee: KOREA INSTITUTE OF SCIENCE AND TECHNOLOGY, Seoul (KR)

(*) Notice: Subject to any disclaimer, the term of this patent is extended or adjusted under 35 U.S.C. 154(b) by 85 days.

(21) Appl. No.: 16/221,585

(22) Filed: Dec. 17, 2018

(65) Prior Publication Data

US 2019/0203260 A1    Jul. 4, 2019

(30) Foreign Application Priority Data

Jan. 3, 2018  (KR) .................. 10-2018-0000901

(51) Int. Cl.
| | | |
|---|---|---|
| *C12Q 1/66* | (2006.01) | |
| *G01N 21/76* | (2006.01) | |
| *C12Q 1/04* | (2006.01) | |
| *G01N 33/573* | (2006.01) | |

(52) U.S. Cl.
CPC ............... *C12Q 1/66* (2013.01); *C12Q 1/04* (2013.01); *G01N 21/763* (2013.01); *G01N 33/5735* (2013.01)

(58) Field of Classification Search
CPC ................................................. G01N 33/5735
See application file for complete search history.

(56) References Cited

U.S. PATENT DOCUMENTS

| | | | | |
|---|---|---|---|---|
| 4,456,380 A | * | 6/1984 | Kondo | G01N 21/253 356/418 |
| 6,218,176 B1 | * | 4/2001 | Berthold | C12Q 1/66 435/287.9 |
| 7,249,671 B2 | | 7/2007 | Riddick et al. | |
| 8,969,072 B2 | | 3/2015 | Robinson et al. | |
| 2011/0091916 A1 | * | 4/2011 | Pan | G01N 21/763 435/8 |
| 2015/0160203 A1 | | 6/2015 | Choi et al. | |

FOREIGN PATENT DOCUMENTS

| | | |
|---|---|---|
| KR | 100727489 B1 | 6/2007 |
| KR | 1020080021641 A | 3/2008 |
| KR | 1020110125510 A | 11/2011 |
| KR | 1020120027359 A | 3/2012 |
| KR | 101280054 B1 | 6/2013 |

OTHER PUBLICATIONS

Sigma-Aldrich, Product Information, Catalog No. FLAA, ATP Bioluminescent Assay Kit, 2015, 3 pages.
Korean Notice of Allowance for corresponding Korean Patent Application No. 10-2018-0000901 dated Jun. 28, 2019, citing the above reference(s).

* cited by examiner

*Primary Examiner* — Bin Shen
(74) *Attorney, Agent, or Firm* — Cantor Colburn LLP

(57) ABSTRACT

Provided is a device for real-time measurement of bacteria. The device for real-time measurement of bacteria includes reaction portions, a support portion configured to support the reaction portions, a rotational shaft configured to transfer the support portion, and a sample supply portion configured to supply a sample to each of the reaction portions, and according to the device for real-time measurement of bacteria, bacteria may be measured in real time through the detection of ATP.

12 Claims, 4 Drawing Sheets

DEVICE FOR REAL-TIME MEASUREMENT OF BACTERIA BY ATP DETECTION

CROSS-REFERENCE TO RELATED APPLICATION

This application claims the benefit of Korean Patent Application No. 10-2018-0000901, filed on Jan. 3, 2018, in the Korean Intellectual Property Office, the disclosure of which is incorporated herein in its entirety by reference.

BACKGROUND

1. Field

One or more embodiments relate to a device for real-time measurement of bacteria.

2. Description of the Related Art

The concentration of fine dust in the air is gradually increasing every year, and as infections by airborne microorganisms and diseases are a frequently occurring issue, national and social interests in the safety of air quality and health risks continue to increase. Currently, air quality is evaluated based on the mass concentration of fine dust particles and the concentration of some chemical species. However, these assessments are merely based on average empirical rules, and it is difficult to accurately determine how they actually affect human health. It is well known the degree to which some chemical species, which are used as reference standards, are a risk to the human body, but it is difficult to accurately know the components of fine dust particles in the air or biological factors. Despite the importance of these indicators in determining the health risks of air quality, clear reference standards for these are not included in the current reference standards, and thus it is more difficult to accurately determine the effect of these components on health.

In addition, home appliances such as humidifiers and the like get contaminated by microorganisms present in the air, through contact, or the like, and thus cases in which health is adversely affected occur rather frequently. Therefore, it is increasingly necessary to measure microorganisms present in the surrounding environment in real time.

Methods of determining the components of fine dust particles or biological factors are well known in the art. The type and concentration of airborne bacteria contained in the air may be easily determined by extracting nucleic acids (DNA or RNA) from a collected air sample and amplifying specific genes that are fingerprints of known airborne bacteria. As another method, the concentration of microorganisms in the air may be easily determined by bringing a collected air sample into direct contact with a solid medium for culturing microorganisms and culturing the sample for 2 to 3 days while maintaining appropriate temperature and humidity to form colonies, and counting the number of the colonies. Such a gene amplification method or culture method is widely used in measuring airborne bacteria, and particularly, the culture method is used as a standard method. However, the gene amplification method requires a reagent for amplifying a gene and a temperature conversion device for controlling various temperature changes for amplification, and a complicated nucleic acid extraction process is required. In the culture method, the prepared solid medium may be directly used, but a culture time of at least one day to one week or more should be secured according to the type of collected bacteria.

Thus, gene amplification and culture methods are not appropriate for real-time or quasi-real-time monitoring of bacteria.

SUMMARY

One or more embodiments include an absorber for detecting bacteria, including a reagent for detecting ATP and a member for immobilizing the reagent.

One or more embodiments include a device for real-time measurement of bacteria including reaction portions, a support portion configured to support the reaction portions, a rotational shaft configured to move the support portion, and a sample supply portion configured to supply a sample to each of the reaction portions.

One or more embodiments include a method of measuring bacteria in real time by using the device for real-time measurement of bacteria.

Additional aspects will be set forth in part in the description which follows and, in part, will be apparent from the description, or may be learned by practice of the presented embodiments.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
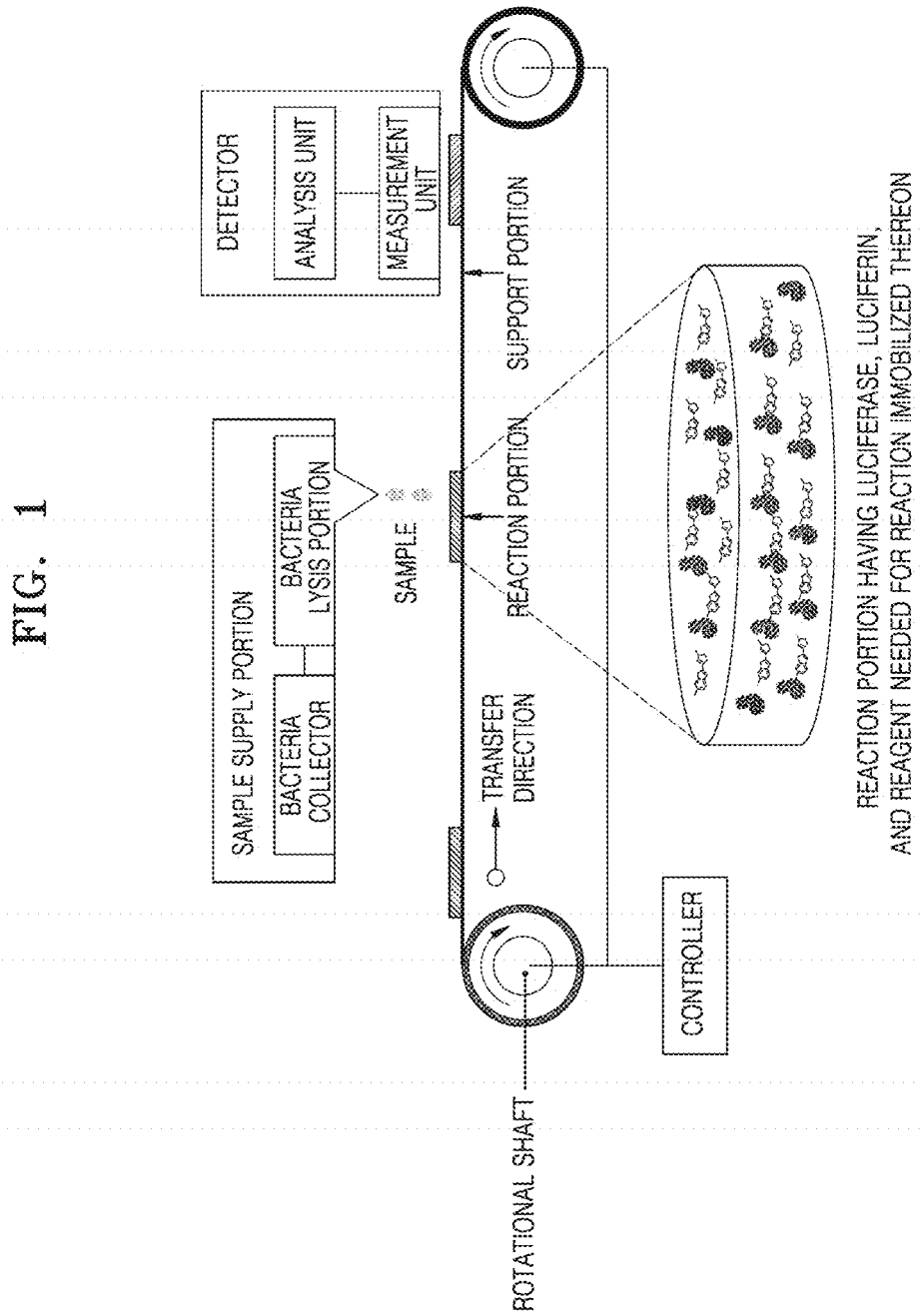
FIG. 1 illustrates an outline of a device for real-time measurement of bacteria.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description.

Hereinafter, embodiments of a device for real-time measurement of bacteria will be described with reference to the accompanying drawings. In the drawings, like reference numerals denote like elements, and the size, thickness, or position of each element may be exaggerated for clarity of explanation.

FIG. 1 illustrates an outline of a device for real-time measurement of bacteria.

Referring to FIG. 1, the device for real-time measurement of bacteria of the present disclosure includes reaction portions, a support portion configured to support the reaction portions, rotational shafts configured to move the support portion, and a sample supply portion configured to supply a sample to each of the reaction portions. According to need, the device may further include a detector configured to detect a reaction occurring in each of the reaction portions.

The sample supply portion may serve to collect bacteria, lyse the collected bacteria, and supply an ATP-containing reaction sample to each reaction portion. The sample supply portion may include, as needed, a bacteria collector and a bacteria lysis portion. In this case, bacteria present in a target to be detected may be collected by the bacteria collector, the collected bacteria may be transferred to the bacteria lysis portion, followed by a bacteria lysis process, thereby providing an ATP-containing sample. For example, the bacteria collector may expose a solution to the air or a fluid and collect bacteria that come into contact with the solution, and the bacteria lysis portion may heat-treat the collected bacteria to be lysed. In addition, bacteria collection and lysis may be performed using methods commonly used in the art. A sample supply amount of the sample supply portion may be controlled by a separate controller, and may be easily adjusted by one of ordinary skill in the art according to the size and moisture absorption capacity of the reaction portions, and the sample supply amount may range from, for example, about 10 μL to about 100 μL.

The reaction portions indicate portions on which reaction reagents for ATP detection are immobilized. For example, the reaction portions may include luciferase, luciferin, and reagents needed for enzymatic reactions, and examples of these reagents include dithiothreitol (DTT), Tris, glycine, $MgSO_4$, ethylenediaminetetraacetic acid (EDTA), and sodium azide. In addition, commercially available reagents for ATP detection or ATP detection reagents commonly used in the art may be used. The reaction portions may include all or some of the reagents for ATP detection. When the reaction portions include some of the reagents for ATP detection, reagents that are not included in the reaction portions may be supplied when a sample is supplied from the sample supply portion, or may be supplied to each reaction portion via a separate reagent supply unit. Luciferase and luciferin are recommended to be stored in a liquid state at a low temperature (4° C. or less), and thus even when the reaction portions include some of the reagents, luciferase and luciferin may need to be included in paper discs.

The reaction portions may be formed of a paper material capable of absorbing moisture; a fibrous material selected from natural fibers including cotton, hemp, wool, and silk, and synthetic fibers including PET-based fibers, acrylic fibers, polyamide-based fibers, polypropylene-based fibers, polyvinyl alcohol-based fibers, polyvinyl chloride-based fibers, polyvinylidene chloride-based fibers, polyurethane-based fibers, polyalkyl paraoxybenzoate-based fibers, and polytetrafluoroethylene-based fibers; or a porous material. In one embodiment, the reaction portions may be in the form of an absorbent for detecting bacteria, which includes a reagent for ATP detection which includes luciferase and luciferin and a member configured to dry and immobilize the reagent.

In the reaction portions, a reaction for ATP detection may be performed, and the ATP detection may be visually confirmed or determined using a separate detector. For example, one of ordinary skill in the art may prepare a reagent that enables a chromogenic reaction, which may be visually confirmed, to occur when ATP is present, or prepare a reagent that enables a luminescence reaction by luciferase to occur, by using knowledge, and measure the luminescence reaction using a separate detection device.

The reaction portions may be located on the support portion. In one embodiment, the reaction portions and the support portion may not be distinguished from each other, or may be formed of the same material.

When the reaction portions are distinguished from the support portion, for example, the reaction portions may be formed of a material capable of absorbing a sample supplied from the sample supply portion, and the support portion may be formed of a non-moisture permeable material or may be coated with a non-moisture permeable material. That is, a liquid sample is absorbed only into the reaction portions and is not leaked into the support portion provided outside the reaction portions. The support portion may be formed of, for example, a plastic film including a synthetic resin coating, vinyl chloride, vinyl acetate, vinyl, vinylidene, polyethylene, polypropylene, or the like.

Each reaction portion may have a surface exposed to the air and another surface attached to the support portion such that the surface exposed to the air may come into direct contact with the lysed liquid sample from collected air. The reaction portions provided on the support portion may be continuously or discontinuously arranged. In the case in which the reaction portions are discontinuously arranged, one of ordinary skill in the art may arbitrarily determine an interval between the respective reaction portions according to a rotation speed of the rotational shafts, a sample supply rate, an ATP detection rate, or the like.

The size of the support portion may be arbitrarily determined by one of ordinary skill in the art, and the support portion may have, for example, a long rectangular tape shape with a width of about 1.5 cm to about 2.0 cm and an unlimited length.

The reaction portions and the support portion may be formed of a flexible material to be wound into a roll form. For example, the reaction portions may be arranged in line with one another on a rotary conveyor belt-type film (support portion) at regular intervals and attached thereto. In addition, opposite ends of the support portion may be wound on respective rotational shafts having the same diameter. The rotational shafts may be connected to a controller so that the rotation speed, number of rotations, rotation pattern, or the like of the rotational shafts may be arbitrarily set by a user. For example, the rotational shafts may be rotated such that each reaction portion is located right below a position where a sample is supplied from the sample supply portion, and after the sample is supplied, the reaction portion may be transferred to the detector, and the amount of ATP present in the sample may be measured. The number of the reaction portions attached to the support portion may be arbitrarily determined by one of ordinary skill in the art depending on the length of the support portion and the interval between the reaction portions, and when all the attached reaction portions are used up by sequentially reacting with the sample, the used reaction portions may be replaced with a roll-type film including the reaction portions and the support portion, in a cartridge form.

A movement distance of the reaction portions each time the rotational shafts rotate once may be the same as a distance between the detector and a position where a sample is supplied from the sample supply portion. Thus, once a reaction portion to which the sample has been supplied is transferred to the detector as the support portion moves, a new reaction portion arranged therebehind is located at the position where a sample is supplied. The rotational shafts may be respectively provided on opposite ends of the support portion, and may be connected to a controller for separate control of an operation thereof.

The detector may include a general device capable of detecting the corresponding reaction according to a reaction pattern of the reaction portions. For example, when a reaction occurring in the reaction portions is a luminescence reaction by ATP, luciferin, and luciferase, the detector may include a luminometer for measuring the luminescence reaction. The detector may include a measurement unit configured to measure the reaction of the reaction portions and an analysis unit configured to analyze measurement results.

According to the real-time bacteria measurement device, when the number of bacteria in a certain volume of a sample increases, the amount of ATP present therein increases, and accordingly, the amount of ATP to be extracted also increases, and thus the number of bacteria present in the sample may be measured according to luminescence intensity.

Hereinafter, the present disclosure will be described in further detail with reference to the following examples. However, these examples are provided for illustrative purposes only and are not intended to limit the scope of the present disclosure.

Example 1. Preparation of Paper Disc-Fixed Conveyor Belt-Type Film Tape 1.1 Preparation of Paper Disc on which Luciferase/Luciferin/Reaction Buffer are Simultaneously Immobilized Luciferase, luciferin, dithiothreitol (DTT), Tris, glycine, $MgSO_4$, ethylenediaminetetraacetic acid (EDTA), and sodium azide were simultaneously immobilized on an ATP reaction paper disc. Particularly, this process is as follows.

A Tris-glycine reaction buffer containing 25 mM Tris, 192 mM glycine, 100 mM $MgSO_4$, 2 mM EDTA, and 2 mM sodium azide was prepared, and the pH of the reaction buffer was adjusted to 7.8. 100 mM DL-dithiothreitol (DTT) was separately prepared. 10 mM D-luciferin was prepared using the reaction buffer. 5 mg/mL of luciferase was prepared using the reaction buffer.

Subsequently, to immobilize the above components on the paper disc, first, 35.6 mL of DI water, 2 mL of the reaction buffer, and 0.4 mL of a DTT solution were mixed. 0.96 mL of the resulting solution as a reference reaction solution was collected and mixed with 0.12 mL of 10 mM luciferin and 0.12 mL of 5 mg/mL luciferase. All reaction components needed for ATP reaction were included in the mixed solution.

Wattmann filter paper was used as the paper disc, and the paper disc was prepared in a circular form having a diameter of about 0.5 cm to about 1.0 cm. 10 μL of the prepared mixed solution, in which luciferase, luciferin, DTT, Tris, glycine, $MgSO_4$, EDTA, and sodium azide were included, was dropped onto the paper disc. Subsequently, a drying process was performed thereon, 10 μL of the mixed solution was dropped again, followed by drying, and 10 μL of the mixed solution was dropped again, and the resulting paper disc was dried in a silica gel-containing sealed container. The dried paper disc was stored at 4° C. to room temperature.

A reaction may occur in the prepared paper disc according to Reaction Scheme 1 below:

<Reaction Scheme 1>

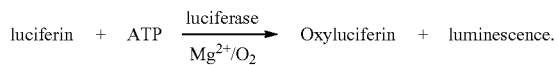

In this mechanism, luciferin, luciferase, and $Mg^{2+}$, which are needed for the reaction, are previously immobilized on the paper disc. There is no need to separately supply $O_2$ because the reaction occurs in a state in which the paper disc is exposed to the air. Thus, when the ATP-containing sample comes into contact with the ATP reaction paper disc, a luminescence reaction occurs immediately. By measuring luminescence intensity, it is possible to determine the presence or absence of ATP and quantify ATP.

1.2 Preparation of Paper Disc-Fixed Conveyor Belt-Type Film

The paper disc prepared according to Example 1 was attached to a cellulose plate tape to manufacture a conveyor belt-type film detector. Particularly, this process is as follows.

ATP reaction paper discs were attached at regular intervals to an adhesive surface of a general cellulose plate tape. An adhesive component remained on a portion of the tape to which the paper discs were not attached, and thus a cellulose plate tape having the same size was perforated with the same size as that of the paper discs and at the same intervals as those at which the paper discs were arranged and adhesive surfaces of the respective cellulose plate tapes were placed opposite each other and attached to each other so that the remaining portion of the adhesive surface did not exist. Consequently, the cellulose plate tape was prepared such that portions thereof to which the paper discs were attached were capable of absorbing moisture and the remaining portion thereof was unable to absorb moisture.

Figure 2:
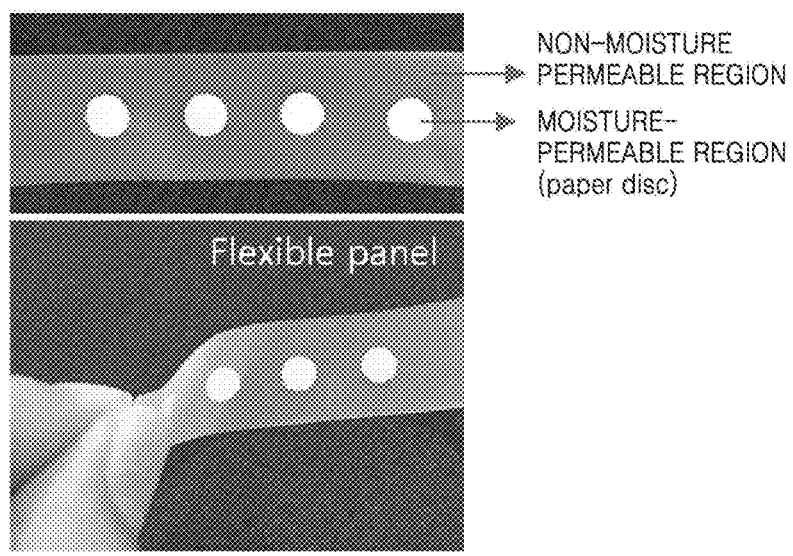
FIG. 2 is an image of an ATP reaction paper disc attached to a conveyor belt film prepared according to an embodiment.

FIG. 2 illustrates a film tape on which the paper discs prepared according to the above example are fixed. As such, a flexible film tape to which paper discs are attached at regular intervals may be formed.

1.3 Configuration of Conveyor Belt of ATP Reaction Paper Disc-Fixed Film

The aforementioned ATP reaction paper disc was composed of a fixed film, and opposite ends of the film were wound on respective rotational shafts. The rotational shafts were connected to a motor so that the number of rotations and a rotation speed were controlled by a motor controller. A distance between the rotational shafts provided on opposite ends of the film was adjusted to about 10 cm.

Subsequently, a sample collector was positioned such that a lysed liquid sample solution from collected air was dropped onto each paper disc on a conveyor belt. The motor controller was operably set such that each paper disc was positioned right below a position where the solution was dropped. The solution with a certain volume is dropped onto the paper disc, and after resting for 10 seconds, the conveyor belt is moved at a certain interval according to rotation of the motor. The paper disc transferred after reacting with the solution is transferred towards a luminometer configured to read the intensity of luminescence emitted in the corresponding reaction, and the amount of airborne bacteria collected for unit hour is measured according to the level of ATP reaction. A new paper disc is positioned at a portion where the solution is subsequently dropped. A time interval at which the solution is dropped may be separately adjusted, and the motor rotates accordingly, allowing the paper disc to be positioned at the position where the solution is dropped.

Example 2. Reactivity Test of ATP Reaction Paper Disc

The ATP reaction paper discs prepared according to Example 1.1 was positioned on a 96-well plate. Subsequently, to test the reactivity of the ATP reaction paper discs,

*E. coli* samples having different concentrations were prepared. Each sample was diluted in 400 µL of sterile water so that from $10^1$ CFU to $10^8$ CFU of *E. coli* were contained, and placed in a 1.5 mL plastic tube for preparation. The 1.5 mL plastic tube was maintained on a heating block preheated to 95° C. for a minimum of two minutes to a maximum of 10 minutes. Thereafter, 100 µL was collected from 400 µL of the sample and added to each well in which the ATP reaction paper disc was placed, and the amount of luminescence was immediately measured using a 96-well luminometer.

Figure 3:
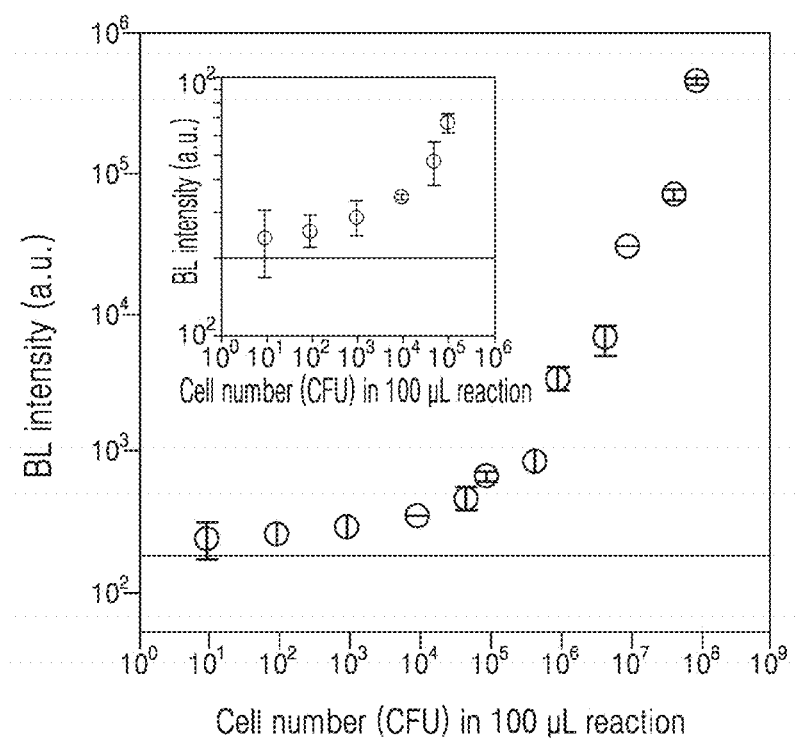
FIG. 3 illustrates results showing bioluminescence (BL) intensity (a.u.) of an ATP reaction paper disc according to the concentration of bacteria.

FIG. 3 illustrates the degree of luminescence of the ATP reaction paper disc according to the concentration of *E. coli*. A gradual increase in luminescence amount from $10^1$ CFU to $10^8$ CFU may be confirmed.

Example 3: Long-Term Storage Stability of ATP Reaction Paper Disc

To confirm the reaction stability of the ATP reaction paper disc of Example 1.1 upon long-term storage, several paper discs were prepared at the same time and stored at room temperature, and each paper disc was used on a specific date to examine reactivity thereof with ATP. In addition, a reaction solution in which luciferase, luciferin, and a reaction buffer, which are needed for ATP reaction, were mixed was prepared as a control, and the reaction solution was stored at room temperature and 100 µL thereof for each case was used on a specific date to examine a luminescence reaction thereof. For the luminescence reaction, a 10 µM ATP solution was used.

Figure 4:
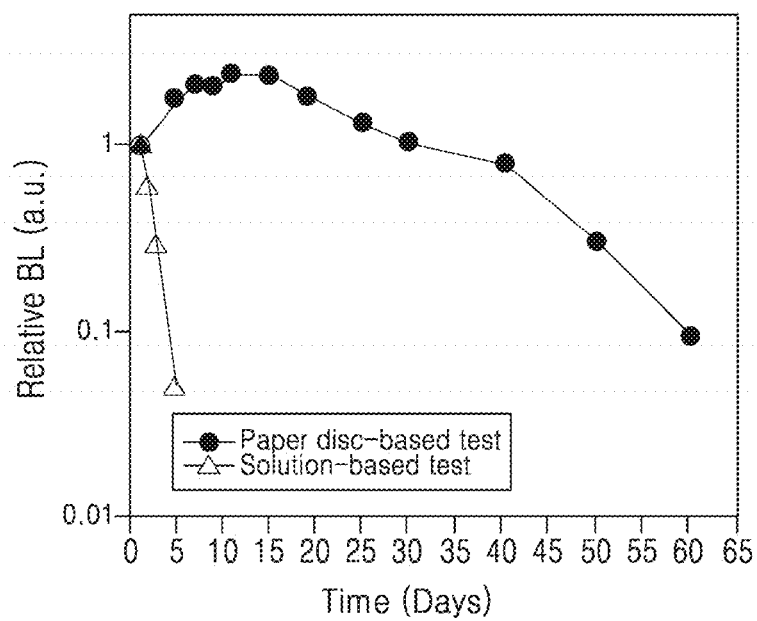
FIG. 4 illustrates the reaction stability of an ATP reaction paper disc over time.

FIG. 4 illustrates the degree of luminescence emitted as a result of a reaction of the ATP reaction paper disc or the solution with 10 µM ATP on specific days. The ATP reaction paper disc did not lose initial luminescence intensity for about 40 days after preparation, or rather exhibited an increase in reaction sensitivity. In contrast, the reaction solution gradually lost initial luminescence intensity and exhibited a rapid decrease to less than 10% of the initial luminescence value, after 5 days.

As is apparent from the foregoing description, according to a real-time bacteria measurement device, there is no need to prepare separate reagents for detecting bacteria, and the like, and time for detecting the presence and concentration of bacteria in a sample may be significantly shortened, thus enabling real-time bacteria measurement.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the disclosure as defined by the following claims.

What is claimed is:

1. A device for real-time measurement of bacteria, the device comprising:
    at least two reaction portions, each having a reagent for adenosine triphosphate (ATP) detection immobilized thereon;
    a flexible support portion configured to support the at least two reaction portions;
    a rotational shaft connected to the support portion and configured to move the support portion; and
    a sample supply portion configured to supply a sample to each of the reaction portions,
    wherein the at least two reaction portions comprise a reagent for ATP detection comprising luciferase and luciferin and a member configured to dry and immobilize the reagent, and
    wherein the at least two reaction portions are arranged on the support portion at regular intervals.

2. The device of claim 1, wherein the reagent further comprises at least one of dithiothreitol (DTT), Tris, glycine, $MgSO_4$, ethylenediaminetetraacetic acid (EDTA), or sodium azide.

3. The device of claim 1, wherein the support portion is formed of a non-moisture permeable material.

4. The device of claim 1, wherein the sample supply portion comprises a bacteria collector configured to collect bacteria and a bacteria lysis portion configured to lyse bacteria.

5. The device of claim 4, wherein the bacteria collector collects airborne bacteria by exposing a solution to the air.

6. The device of claim 4, wherein the bacteria lysis portion performs heat treatment on the collected bacteria.

7. The device of claim 1, wherein the member configured to dry and immobilize the reagent is at least one of paper, natural fiber, synthetic fiber, or porous material.

8. The device of claim 1, wherein the support portion and the at least two reaction portions are capable of being wound in a cylindrical form according to rotation of the rotational shaft.

9. The device of claim 1, wherein the support portion and the at least two reaction portions are detachable from the device for real-time measurement of bacteria.

10. The device of claim 1, further comprising a detector configured to detect a reaction occurring in each of the reaction portions.

11. The device of claim 10, wherein the detector is a luminometer.

12. A method of measuring bacteria in real time by using the device of claim 1, the method comprising:
    supplying a sample from a sample supply portion to a first reaction portion;
    moving a support portion using a rotational shaft, thereby placing a second reaction portion at a position where the second reaction portion is able to receive the sample from the sample supply portion;
    detecting ATP present in the first reaction portion; and
    repeating the above processes at least once by using at least two reaction portions.

* * * * *